United States Patent [19]

Lee et al.

[11] Patent Number: 4,595,594
[45] Date of Patent: Jun. 17, 1986

[54] PROCESS FOR PREPARING INTENSIFIED CHEESE FLAVOR PRODUCT

[75] Inventors: Chang R. Lee, Yonkers; Chifa F. Lin, Irvington; Nicholas Melachouris, White Plains, all of N.Y.

[73] Assignee: Stauffer Chemical Company, Westport, Conn.

[21] Appl. No.: 533,821

[22] Filed: Sep. 19, 1983

[51] Int. Cl.$^4$ .............................. A23C 9/12
[52] U.S. Cl. ........................ 426/35; 426/36; 426/38; 426/39
[58] Field of Search ................ 426/35, 36, 38, 39

[56] References Cited

U.S. PATENT DOCUMENTS

| | | | |
|---|---|---|---|
| 2,965,492 | 12/1960 | Bauman et al. | 99/116 |
| 3,446,627 | 5/1969 | Noznick et al. | 99/115 |
| 3,469,993 | 9/1969 | Pangier | 426/35 |
| 3,689,286 | 9/1972 | Luksas | 99/115 |
| 3,975,544 | 8/1976 | Kosikowski | 426/35 |
| 4,119,732 | 10/1978 | Kratochvil | 426/38 |
| 4,172,900 | 10/1979 | Dooley | 426/35 |
| 4,244,971 | 1/1981 | Wargel et al. | 426/35 |
| 4,313,962 | 2/1982 | Sternberg et al. | 426/35 |
| 4,379,170 | 4/1983 | Hettinga et al. | 426/40 |
| 4,401,679 | 8/1983 | Rubin et al. | 426/36 |

OTHER PUBLICATIONS

Kirk–Othmer–Encyclop. of Chem. Tech., vol. 15, 3rd edit. p. 523.
Dairyland Food Lab–Technical Bull. No. 0101, pp. 1–3.
Rohm–Haas–Enzyme Products–Rhozyme–Proteases, pp. 1–8.
Kilara, A. and Shahani, D. M., "Lactic Fermentations of Dairy Foods and Their Biological Significance", J. Dairy Sci. 61, pp. 1793–1800, (1978).
Alm, L., "Effect of Fermentation on Milk Fat of Swedish Fermented Milk Products", J. Dairy Sci. 65, pp. 521–530, (1982).
Rao, D. V. and Murthy, M. K. R., "Production of Monocarbonyl Compounds During Ripening of Cream by Lactic Cultures", Milchwissenschaft 37 (10), pp. 601–603 (1982).
Chandon, R. C., Gordon, J. F. and Walker, D. A., "Dairy Fermentation Processes", Process Biochemistry, Feb. 1969, (pages unknown).
Sood, V. K., et al., "Accelerated Cheddar Cheese Ripening by Added Microbial Enzymes", J. Dairy Sci., 62, No. 12, pp. 1865–1872 (1979).
Kosikowski, F. W., et al., "Changes in Cheddar Cheese by Commercial Enzyme Preparations", J. Dairy Sci. 58, No. 7, pp. 963–970 (1975).
Law, B. A., et al., "Accelerated Cheese Ripening with Food Grade Proteinases", J. Dairy Res. 49, pp. 137–146 (1982).
Law, B. A., "Accelerated Ripening of Cheese", Dairy Industries International, 45 (5), pp. 15, 17, 19, 20, 22 and 48 (1980).

*Primary Examiner*—Sam Rosen
*Attorney, Agent, or Firm*—Paul J. Juettner

[57] ABSTRACT

A cheese flavor product can be prepared by incubating cheese or cheese curd with a lipase enzyme, preincubating the mixture to partially digest the cheese or curd, incubating the partially digested cheese to develop the flavor and admixing cream with the product after preincubation or incubation. The product has an intense cheese flavor which is usable as an additive to cheese or imitation cheese to improve the flavor characteristics thereof.

28 Claims, No Drawings

PROCESS FOR PREPARING INTENSIFIED CHEESE FLAVOR PRODUCT

The present invention relates to a product having a highly intensified cheese flavor and a method of preparing the same.

Flavor development in cheeses such as Cheddar, Colby, Jack and Monterey generally require storage periods ranging from one month to over one year for the sharper flavors (sharp Cheddar required 9-12 months aging). Storage cost and interest add significantly to the final cost of the cheese product.

For uniformity and to obtain a proper blend of cheese flavors, a cooked cheese process was developed wherein cheeses of various ages are ground, melted and emulsified until a uniform plastic mass is formed. The cheese is then formed into loaves or slices. Depending on the cheese content, moisture content and fat level, these products are termed process cheese (maximum moisture 40%, and minimum fat level 47%), process cheese food (maximum moisture level 44%, minimum cheese level 51% and maximum fat level 23%) and process cheese spread (moisture level 44-60%, minimum cheese level 51% and minimum fat level 20%). Process cheese products not corresponding to these limits are generally termed imitation cheese. These will be collectively referred to as process cheese.

Since aged cheese is responsible for cheese flavor, process cheese uses blends of aged and young or green cheese. In order to reduce the costs of using aged cheese, the industry has experimentally added flavor components individually and in admixtures to process cheese with little real success. The industry has also developed cheese products with intensified flavor such as enzyme modified cheese to provide the flavor components.

Accelerated cheese aging has been accomplished by adding various enzymes to cheese curd or young cheese (U.S. Pat. No. 4,119,732; Accelerated Cheddar Cheese Ripening by Added Microbial Enzymes, V. K. Sood et al., J. Dairy Sci. 62 No. 12, pp. 1865-1872 (1979); Changes in Cheddar Cheese by Commercial Enzyme Preparations, F. V. Kosikowski et al., J. Dairy Sci., 58 No. 7 pp. 963-970 (1975); Accelerated Cheese Ripening with Food Grade Proteinases, B. A. Law et al., J. Dairy Res. 49 pp. 137-146 (1982); Accelerated Ripening of Cheese, B. A. Law, citation unknown; Microbial Proteinases as Agents for Accelerated Cheese Ripening, B. A. Law et al., J. Soc. Dairy Tech 35 No. 2 (1982) pp. 75-76).

For example, U.S. Pat. No. 4,172,900 teaches preparing a cheese with ten times the $C_2$-$C_{10}$ fatty acid content by adding proteolytic and lipolytic enzymes (calf, kid or lamb throat tissue lipase) to cheese curd just after salting the curd. The lipases are commercially available under the brand names STALASE and CAPALASE. The protease can be obtained from *A. flavus oryzae* and *B. subtilis*.

U.S. Pat. No. 3,975,544 discloses adding lipase and neutral protease enzymes to cheddared cheese to improve the cure rate.

In U.S. Pat. No. 3,789,182, a powdered cheese flavoring material is provided by treating a cheese/fat blend with a lipolytic enzyme, combining the enzyme treated cheese with a protein material (whey, buttermilk, skim milk, soy protein and the like) and drying the combined material. Lipase from the throat tissue of calves, lambs and kids was found to be effective.

U.S. Pat. No. 4,244,971 discloses a cheese product for process cheese prepared by prefermenting a blend of a proteolyzed milk protein concentrate, lipase treated cream and milk protein concentrate. After fermentation a cheese culture was added to prepare a cheese product.

U.S. Pat. No. 2,965,492 teaches preparing a dried cheese product by fermenting milk in the presence of enzymes and drying the product without separating the whey.

British Pat. No. 2,008,923 discloses a process for preparing imitation cheese by treating portions of skim milk with a proteolytic enzyme and a lipolytic enzyme followed by adding two of the portions to skim milk to form curd.

U.S. Pat. No. 3,446,627 relates to a process for rapidly manufacturing cheese by precipitating the milk protein in the form of a slurry, adding bacteria of the type commonly found in cheddar cheese and then allowing the bacteria to ripen in a fluid medium for up to approximately ten days. At the conclusion of the ten days, the material is dried. This patent is illustrative of a fermentation in a slurry system at a total solids of 10 to 30 percent.

SUMMARY OF THE INVENTION

In accordance with the present invention, an intensified cheese flavor product can be prepared by incubating cheese or cheese curd with a lipase enzyme preferably in combination with a neutral protease enzyme, allowing the enzyme(s) to partially digest the cheese as evidenced by a smooth, easily agitatable mixture, adding cream and incubating until the desired intensified cheese flavor is obtained. By this procedure a product having an intensified cheese flavor is obtained which can be used in combination with cheese to provide an aged cheese flavor without the expense of aging or in combination with other ingredients to prepare an imitation cheese. The intensity of the cheese flavor is such that the product must be diluted prior to use.

DETAILED DESCRIPTION OF THE INVENTION

The present invention is directed to preparing a product having an intensified cheese flavor using cheese curd or cheese as a starting substrate. The cheese or cheese curd can be prepared by any known method, generally by incubating a casein source such as whole milk or skim milk with a lactic acid producing bacteria and a rennet enzyme. The cheese is preferably young cheese (0-30 days) though partially aged cheese, i.e., 30 to 90 days can also be used. Partially aged cheese will provide more flavor components though its use is not required.

Cheese curd can also be utilized wherein the same is prepared by any standard known method. As illustrative, pasteurized whole milk or skimmed milk after cooling to a temperature which will not adversely affect or damage added bacteria (such as about 31° C.) can be inoculated with any lactic acid producing bacteria which are well known to those skilled in the art for this purpose. Especially favorable results have been found using a blend of about 0.01% to about 0.20% based on a total $10^{10}$ viable cells per gram of a commercial culture containing *S. lactis* and *S. cremoris* in a ratio ranging from about 1:9 to about 9:1 and preferably of 1:1 and from about 0% to about 0.5% of *L. casei* based on $10^8$ viable cells per gram. The amount of culture used is dependent on the cell count and volume can be adjusted accordingly. Preincubation of the culture in a starter medium has been found desirable to increase the cell count. The inoculated milk is incubated at a temperature sufficient to allow effective growth of the bacteria. A temperature ranging from about 20° C. to about 40° C. and more preferably from about 28° C. to about 34° C. has been found to be effective. The whole milk is incubated for a period of time sufficient to provide from about 0.18% to about 0.20% titratable acidity calculated as percent lactic acid.

An effective time to develop the above titratable acidity ranges from about 20 to about 90 minutes and preferably from about 30 to about 40 minutes. After the initial growth of the bacteria has been undertaken, the incubated milk is inoculated with an amount of a coagulant such as calf rennet or rennin from any desirable source sufficient to effect coagulation of the milk. These amounts are well known to the skilled artisan. The milk is further incubated for a period of time and at a temperature sufficient to coagulate the milk. Temperatures of from about 20° C. to about 40° C. and preferably from about 28° C. to about 34° C. for a period of time ranging from about 20 to about 90 minutes, and preferably from about 30 to about 40 minutes have been found to be effective.

Following the coagulation, the coagulant can be cut into curd to assist in whey removal using any device adapted for that purpose, such as a knife, or a cheese knife which is a series of intersecting wires forming rectangles of desired size. The whey can then be partially expressed and drained using well known art recognized techniques. Incubation is continued until a pH of about 4.9 is obtained. Most of the remaining whey is drained and expressed using known techniques. The curd can be salted to assist in draining of the whey or it can be salted after draining of the whey. Salting in an amount of up to about 3% based on the weight of the cheese curd has been found to be effective. Heating can also be used to express whey from the curd.

If desired, the coagulant can be utilized in the process of the invention without removing the whey. It is preferred in so using the coagulant, that the coagulant be homogenized to form a mass of suspended particles in the whey.

The cheese or cheese curd is reduced in particle size to a size sufficient to provide a large surface area for the subsequent effective incubation of the cheese with an enzyme. For young cheese, this can be accomplished by shredding or grinding. The same can also be accomplished by melting the cheese and admixing the enzymes with the melted cheese at a temperature below that which serious damage would occur to the enzyme. In order to develop the desired flavor over the incubation period, it has been found desirable to add from about 0 to about 0.5% *L. casei* based on $10^6$ viable cells per gram of cheese. In connection with the curd, the curd can be cut into sizes of desired shape such as cubes or particles of irregular shape. Preferably, particles having a volume of approximately one cubic centimeter are preferred. Larger sizes can be utilized though this requires an extensively longer time for enzyme reaction.

The present invention can be utilized to prepare flavor products for any type of cheese including the Cheddar type cheeses and the Italian cheeses. The initial cheese base utilized will dictate the flavor of the final product to a large degree. If desired, blends of cheese or cheese curd can be utilized if a mixed flavor is desired. Preferably, the cheese or cheese curd is of the Cheddar variety and this will be utilized for purposes of explanation hereinafter though it is understood that the explanation will apply equally to other types of cheese or mixtures thereof.

The cheese or cheese curd is inoculated with a lipase enzyme. The lipase can be derived from animal or microbial sources. Included within the term "animal lipase" is the preferred gastric lipase pancreatin. Pregastric lipases such as those obtained from the throat or tongue tissue of lamb, kid, calf, or goat as described and illustrated in U.S. Pat. No. 2,794,743 can also be used. Generally, these latter enzymes are not available commercially in strength sufficient to be utilized to any practical degree. Preferably, a mixture of gastric and pregastric enzymes are utilized. Microbial lipase can be obtained from a fungal source, illustrated by *Mucor miehei* and a bacterial source which can be illustrated by *B. subtilis*. Preferably the lipase is a gastric lipase used in combination with either a pregastric or microbial lipase or both.

While the lipase can be utilized alone, it has been found that better results are obtained when utilizing the lipase in combination with a neutral protease. A neutral protease is an enzyme which attacks protein having its maximum activity at about neutral pH. A neutral protease when used alone provides a bitter cheese flavor. The neutral protease can be derived from animal, vegetable or microbial (bacterial and fungal) sources. The preferred neutral protease is a bacterial protease such as the neutral protease from *B. subtilis* available as NEUTRASE ™ from Novo. It is also pointed out that pancreatin, an animal derived enzyme, contains not only lipase but also proteases. For that reason, pancreatin provides an additional benefit. Vegetable neutral protease can be illustrated by papain and fungal neutral protease can be derived from the genus Aspergillus such as *A. oryzae, A. flavus,* and *A. niger.* Fungal neutral protease can be illustrated by Fungal Protease from Miles Laboratories. The neutral protease can be of one type or a blend of various types.

The most effective results have been found when using a three component enzyme system, i.e., a gastric lipase, a pregastric lipase and a neutral protease combination. The preferred combination is pancreatin in an amount sufficient to provide a lipase activity from about $10 \times 10^3$ to about $30 \times 10^3$ I.U. per gram of cheese or curd; throat or tongue tissue of lamb, kid, calf or goat in an amount sufficient to provide a lipase activity from about $0.5 \times 10^4$ to about $2 \times 10^4$ I.U. per gram of cheese or curd; and a bacterial protease from *B. subtilis* in an amount sufficient to provide a protease activity from about $2 \times 10^{-4}$ to about $5 \times 10^{-4}$ Anson units per gram of cheese or curd. The amount of enzyme added is dependent on the enzyme activity.

One International Unit (IU) of lipase activity is defined as the quantity of lipase that liberates the equivalent of 1 micromole of acid ($H^+$) per minute from a substrate, under the condition of assay. One Anson unit (Au) is the quantity of proteolytic enzyme which, under standard conditions, digests hemoglobin at an initial rate liberating per minute an amount of TCA soluble product that gives the same color with phenol reagent as one milliequivalent of tyrosine.

The cheese or cheese curd to which has been added the enzyme mixture is then incubated for a sufficient period of time to allow the cheese to partially digest. This is evidenced by a looser or thinner texture in the incubate. Agitation is much easier than before. This preincubation step should be conducted for a period of time sufficient to provide a curd with a consistency similar to that of thick paste. The preincubation period generally requires from about 5 to about 60 minutes.

The partially incubated cheese is then admixed with cream. By "cream" is meant any butterfat containing product having more than about 12% and less than about 100% butterfat and preferably from about 15% to about 40% butterfat, the percentage being by weight/weight based on the weight of the cream. The term "cream" is intended to not only include natural products separated from milk, but also modified products. The term "cream" is intended to include products such as those identified by the terms "heavy cream" (from about 35% to about 40% butterfat), "light cream" (from about 20% to about 25% butterfat), "half-and-half" (about 12% butterfat), and "anhydrous cream". The term "cream" is also intended to include modified products such as butter, butterfat and cultured dairy products such as sour cream.

Sour cream is a well known and defined dairy product. Basically, fresh cream with 19% butterfat (after pasteurization) is inoculated with a lactic acid starter (*S. lactis* and *L. citrovorum*) until the desired acidity is achieved. Chilled sour cream generally has a pH of from about 4.2–4.4. The process and variations are outlined in Cheese and Fermented Milk Foods, F. Kosikowski, 1966, Edward Brothers Inc., Ann Arbor, Mich. The acidity of the sour cream is adjusted to a pH sufficient to avoid retarding the enzyme system, i.e., a pH of 5.5±0.3, with a food grade base such as sodium hydroxide.

Pure butterfat can be used in the invention but only after emulsification of the butterfat in a small quantity of water and with appropriate emulsifying agents if necessary, as is well known to a skilled artisan.

It is intended that the term "cream" include not only single products but blends of various cream products such as those mentioned hereinbefore. The type of cream utilized can have an effect on the ultimate flavor provided by the product of the invention. Preferably, the cream source is a heavy cream having a butterfat content ranging from about 35% to about 40% butterfat. It is also desirable to use sour cream and combinations thereof. The cream is added to the cheese curd with sufficient agitation to provide uniform admixture throughout the cheese or cheese curd.

The cream is used in an amount sufficient to provide a quantity of butterfat for the lipase enzyme sufficient for producing from about 8 to about 12 millimoles total free fatty acids per 10 grams mixture of cream and curd/cheese after a 48 hour incubation. The amount of cream utilized is based on the butterfat content. Preferably the cream which is added provides at least 4% butterfat and more preferably from about 11% to about 15% butterfat, the percentages being based on the weight of the initial cheese or cheese curd. Products low in butterfat content are less preferred since the addition of the amount needed to provide the desired butterfat content will extensively dilute the incubation mixture as well as adding extraneous materials.

The blend of cheese, enzymes, and cream is then incubated for a period of time sufficient and at a temperature which is conducive to the development of the intensity of the cheese flavor sought. Incubation is generally conducted with periodic agitation for a period of time ranging from about 30 hours to about 72 hours and preferably from about 40 to about 56 hours. The temperature for incubation generally ranges from about 25° C. to about 40° C. and preferably from about 32° C. to about 38° C. Selection of the temperature conducive to enzymatic hydrolysis depends on the enzymes utilized.

After incubation, the cheese flavor product can be heated at a temperature and for a period of time sufficient to inactivate the enzymes, but insufficient to develop off-flavor components. A temperature ranging from about 80° C. to about 121° C. and preferably about 90° C.±5° C. has been found to be effective. Heating is preferably conducted for a period of time ranging from about 1 second to about 40 minutes depending on temperature (higher temperatures—shorter times). After cooling to room temperature, the product can be packaged and stored in a refrigerator.

After incubation and before enzyme inactivation, the cheese flavor can also be further modified to better or improve the flavor characteristics of the product. To more fully round out the flavor characteristics of sharp Cheddar cheese, it has been found desirable to add to the incubated cheese flavor any or all of from about 2.5% to about 4% salt; from about 0.5% to about 1.2% ammonium phosphate; from about 1.0% to about 2.5% of a food grade acid such as acetic acid (glacial acetic acid); and from about 50% to about 100% of cream (as defined hereinbefore), fermented milk, fermented cream or a combination thereof. The aforegoing percentages are based on the weight of the cheese or cheese curd initially used in the product. The fermented whole milk can be prepared by pasteurizing whole milk such as by heating at 90° C. for 5 seconds followed by incubating the milk with an appropriate lactic acid producing bacteria preferably *L. casei*, though other bacteria known for this purpose can also be used, at a temperature appropriate for its growth which in this case ranges from about 25° C. to about 40° C. for an appropriate period of time which is illustrated by the range of from about 40 hours to about 56 hours. Other conditions for fermentation are well known to one skilled in the art. In place of the fermented milk or as a portion thereof, one could substitute a cultured cream product such as sour cream. The cream is used in an amount sufficient to provide at least about 11% butterfat and preferably from about 11% to about 20% butterfat (the percentage being by weight based on the weight of the cheese or cheese curd). These ingredients can also be added after enzyme inactivation.

The product of the invention is characterized by an intense cheese flavor. The cheese flavor is sufficiently intense that the product cannot be used alone like cheese. The product of the invention is used in admixture with other materials such as cheese to prepare a cheese flavored product or other dairy ingredients such as casein and whey to prepare an imitation cheese. For example, 17% of the aged (sharp) cheese in a processed cheese spread formulation can be replaced with the product of the invention which has been diluted from about 5 to about 20 times with barrel and/or young cheese without substantial loss in flavor thus allowing a decrease in the amount of aged cheese used in preparing that product. The cheese flavor can also be used as a coating for snack foods or as a cheese flavor in prepared foods, in cheese flavored sauces or soups and the like. The cheese flavor product of the invention can be used with other dairy and vegetable protein materials to form an imitation cheese.

The invention will be further illustrated in the Examples which follow.

EXAMPLE 1

Sixty day old Cheddar cheese was sliced into small pieces in a food processor and melted by heating to a temperature of 50°-55° C., the cheese being actively stirred during melting. After melting, the cheese was cooled to about 35° C. Two percent pancreatic lipase (Miles Laboratories) in powdered form with an activity of about $12 \times 10^5$ International Units per gram enzyme was admixed into the cheese. One percent of a lipase from the edible tissue of kid's glands (Capalase K—Dairyland Food Laboratories) in powdered form and 0.05% of a bacterial enzyme (Neutrase 0.5 L—Novo Laboratories) in liquid form were blended in sequentially. The cheese was mixed until the cheese texture was loosened and became pasty—about 1 hour. Sour cream having a butterfat content of about 21% in an amount of about 25% W/W of the cheese with a preadjusted pH of about 5.5 was blended thoroughly into the cheese.

The inoculated cheese was then incubated at about 35° C. for about 48 hours. For control purposes, a sample was taken after 6, 12, 24, 30, 36 and 48 hours incubation. The incubated cheese was then heated to about 90°-95° C. for 30 minutes to inactivate the enzyme. The product was cooled to room temperature, packaged and stored in a refrigerator.

The samples collected at various incubation periods were evaluated for flavor against a commercial enzyme modified cheese flavor product (Dairyland CPF 7103). Since the flavor of the samples as well as the commercial product was quite intense, they were diluted 10 times in a starch-milk base model system simulating cheese sauce before evaluation. The starch-milk base was prepared by heating whole milk containing 5% starch to about 60° C. The test samples and the commercial enzyme modified cheese flavors were added to the starch-milk base at about 40° C. After mixing well and cooling to from about 25° to about 30° C., the flavored starch-milk base samples were evaluated for flavor. The 30, 36 and 48 hour samples were comparable in flavor and flavor intensity to the diluted commercial product, whereas the 6, 12 and 24 hour samples were less intense.

To improve the flavor, 0.8% glacial acetic acid was added to the 48 hour sample. The sample containing 0.8% glacial acetic acid was further evaluated in an imitation cheese formulation as shown in Table I below against the commercial product (Dairyland CPF 7103). The use level in the formulation was 3%. A flavor panel found that the imitation cheese made with the 48 hour sample containing 0.8% glacial acetic acid was close in both flavor and flavor intensity to that containing the commercial product.

TABLE I

Imitation Cheese Formulations

| Ingredients | With Product of Example 1 | With Commercial Product |
|---|---|---|
| Sodium/Calcium Caseinate | 17.78% | 17.78% |
| Salt | 1.71% | 1.71% |
| Sodium Citrate | 2.43% | 2.43% |
| Disodium Phosphate, duohydrate | 0.49% | 0.49% |
| Glucono-delta-lactone | 1.71% | 1.71% |
| Whey (dry) | 4.88% | 4.88% |
| Oil (Durkee 321)* | 18.5% | 18.5% |
| Water | 49.5% | 49.5% |
| Product of Example 1 | 3.0% | — |
| Commercial Product | — | 3.0% |

*Plastic shortening-soy bean oil base.

EXAMPLE 2

One hundred ninety liters (50 gallons) of pasteurized fresh whole milk was placed in a tank and the termperature adjusted to 31° C. (88° F.). To this was added 0.15 liters (0.042 gallons) of a 50/50 mixed culture of *S. lactis* and *S. cremoris* (Hansen's DVS culture) and 0.50 liters (0.132 gallons) of an *L. casei* broth containing about $1 \times 10^8$ cells per gram.

The inoculated milk was incubated under continuous agitation for 35 minutes at 31° C.

Calf rennet extract (single strength) in an amount of about 0.04 liters (0.01 gallons) and diluted 1:10 with distilled water was introduced into the tank. After agitation for 2 minutes, agitation was stopped and incubation continued for 1 hour at 31° C.

After determining the strength of the curd with a spatula, the coagulum was cut into irregular shaped pieces of approximately 1 cubic centimeters using a knife. The curd was then cooked slowly under agitation using steam in the jacket of the tank until a peak temperature of 38° C. (100° F.) in 30 minutes (1° C. rise per 5 minutes) was reached. The product was further incubated for 45 minutes at 38° C.

Sufficient whey was drained until the cooked curds appeared on the surface of the whey. Incubation was continued at 38° C. with agitation until a pH of 4.9 was reached. The whey was drained from the curd.

The fresh curd with a solids content of about 47% was weighed and put into a reactor tank. Two percent flaked salt and 0.05% bacterial protease (Neutrase) was added to the curd. After mixing for 5 minutes, 2% powdered pancreatic lipase wetted with cream was added to the curd. After mixing for 10 minutes, 1% water wetted powdered kid glandular lipase (Capalase K) was added to the curd and agitation was continued until the curd texture loosened to an homogeneous paste. The percentage of each of the enzymes and salt is by weight based on the weight of the drained curd.

The reactor tank was covered tightly and incubated for 48 hours at 35° C. with periodic agitation (once per hour).

At the conclusion of the incubation, there was added 3.3% salt, 0.8% ammonium phosphate dibasic, 30% butter and 70% half-half cream having a butterfat content of from about 10.5% to about 12%, the percentage being by weight based on the weight of the curd.

The mixture was heated rapidly to 90°-95° C. and held for 30 minutes. The mixture was cooled to about 50° C., 1.0% glacial acetic acid was admixed and the mixture further cooled to about 15°-25° C. The mixture was sealed and agitated during the heating, holding and cooling steps. The product was packaged in polylined containers and stored in the refrigerator.

The product was evaluated at a 2% level in unflavored process cheese spread in a loaf form as shown in TABLE II. The process cheese spread prepared with the above product evidenced a tangy, cheesy flavor and had good flavor balance in comparison to unflavored process cheese spread control with a mild Cheddar flavor.

TABLE II

| Ingredients | Process Cheese Spread Formulations | |
|---|---|---|
| | Control (Without Flavor Product) | With the Product of Example 2 |
| Barrel American Cheese (unaged) | 63.94% | 61.94% |
| Disodium Phosphate, duohydrate | 2.25% | 2.25% |
| Salt | 0.70% | 0.70% |
| Nonfat Dry Milk | 5.45% | 5.45% |
| Whey (dry) | 6.00% | 6.00% |
| Butter | 1.25% | 1.25% |
| Water | 10.41% | 10.41% |
| Steam | 10.00% | 10.00% |
| Product of Example 2 | — | 2.00% |

EXAMPLE 3

The procedure of Example 2 for preparing the curd and draining the whey was repeated. After weighing the curd (solids content of about 47%), 2% flaked salt and 0.05% bacterial protease (Neutrase) was added to the curd. After agitation for 5 minutes, 2% (dry basis) pancreatic lipase powder wetted with heavy cream (38% butterfat) was added to the curd. After agitation for 10 minutes, 1% (dry basis) kid glandular lipase powder (Capalase K) wetted in heavy cream was added to the curd. Agitation was continued until the curd texture loosened to an homogenous paste. The total amount of heavy cream used in wetting the two powder enzymes is 33.3%, the percentages above being based on the weight of the curd. Wetting was conducted immediately before addition.

The curd was incubated quiescently for 48 hours at 35° C. in a covered reactor. At the end of the incubation, 3.3% salt, 0.8% ammonium phosphate dibasic and 66.7% heavy cream was added, the percentages being by weight based on the weight of the curd.

The mixture was rapidly heated to about 90°–95° C. and held for 30 minutes. After cooling to about 50° C., 1% glacial acetic acid was admixed into the product. The product was cooled to 15°–25° C., packaged in polylined containers and stored in the refrigerator.

The product was evaluated at a 0.75–1.0% use level in unflavored process cheese spread (64% barrel cheese—no sharp Cheddar cheese) in loaf form as shown in TABLE III. The commercial enzyme modified cheese flavor product (Dairyland Foods CPF 7103) was used at a 1% level in an unflavored process cheese spread. The control cheese spread without enzyme modified cheese flavor product was made with a 47/17 ratio of barrel and sharp Cheddar.

The cheese spread made with the product of this example was comparable in flavor and flavor intensity to the control cheese spread as well as to that made with the commercial product.

TABLE III

| Ingredients | Process Cheese Spread Formulations | | |
|---|---|---|---|
| | With the Product of Example 3 | With Commercial EMC | Control |
| Barrel American Cheese | 63.19% | 62.94% | 46.94% |
| Sharp Cheddar Cheese | — | — | 17.00% |
| Disodium Phosphate, duohydrate | 2.25% | 2.25% | 2.25% |
| Salt | 0.70% | 0.70% | 0.70% |
| Nonfat Dry Milk | 5.45% | 5.45% | 5.45% |
| Whey (dry) | 6.00% | 6.00% | 6.00% |
| Butter | 1.25% | 1.25% | 1.25% |
| Water | 10.41% | 10.41% | 10.41% |
| Steam | 10.00% | 10.00% | 10.00% |
| Flavor Product of Example 3 | 0.75% | — | — |
| Commercial Enzyme Modified Cheese | — | 1.00% | — |

What is claimed is:

1. A process for preparing a cheese flavor product comprising:
    (a) innoculating a cheese or cheese curd prepared from milk with a gastric lipase enzyme in an amount above about 9000 International Units of lipase activity per gram of cheese or cheese curd;
    (b) admixing the product of Step (a) before, during, or after innoculation or a combination thereof with an amount of cream sufficient to provide at least about 4% butterfat based on the weight of the initial cheese or cheese curd said product of steps (a) and (b) having a thinner texture than the cheese or cheese curd alone without whey;
    (c) incubating the product Step (b) for a period of time sufficient to provide a product having an intensified cheese flavor; and
    (d) inactivating the enzyme.

2. The process of claim 1 wherein said cheese or cheese curd is comminuted to a particle size of less than about three cubic centimeters.

3. The process of claim 1 wherein said cream is added to the product of step (a) before or during inoculation.

4. The process of claim 1 wherein the lipase is pancreatin.

5. The process of claim 1 wherein the lipase is a blend of gastric and pregastric lipases.

6. The process of claim 5 wherein the gastric lipase is pancreatin and the pregastric lipase is derived from the throat or tongue tissue of kid, lamb, calf or goat.

7. The process of claim 1 wherein the lipase is used in combination with a neutral protease enzyme.

8. The process of claim 7 wherein the neutral protease is a neutral bacterial protease.

9. The process of claim 1 wherein the lipase enzyme is pancreatin and is used in combination with a pregastric lipase and a neutral bacterial protease.

10. The process of claim 9 wherein the pancreatin is used in an amount of more than about 9000 International Units of lipase activity per gram of cheese or cheese curd; the pregastric lipase is used in an amount of more than about 1000 International Units of lipase activity per gram of cheese or cheese curd; and the neutral bacterial protease is used in an amount of more than about $2 \times 10^{-5}$ Anson units per gram of cheese or cheese curd.

11. The process of claim 1 wherein the cream is heavy cream having at least 35% butterfat.

12. The process of claim 1 wherein the cream is sour cream.

13. The process of claim 1, wherein the cheese of step (a) is inoculated with *L. casei*.

14. The process of claim 1 wherein the material inoculated is cheese curd.

15. The process of claim 14 wherein said cheese curd is prepared by:
   (a) incubating pasteurized milk which has been inoculated with lactic acid producing bacteria;
   (b) inoculating the product of step (a) with a rennin-containing coagulum and incubating the product to form a coagulum;
   (c) cutting the coagulant into curd and partially removing whey;
   (d) holding the curd until a pH of below 5 is developed; and
   (e) removing the whey.

16. The process of claim 15 wherein the lipase is a blend of gastric and pregastric lipases.

17. The process of claim 15 wherein the genus of said bacteria is selected from the group consisting of *Streptococcus* and *Lactobacillus*.

18. The process of claim 15 wherein said bacteria includes *L. casei*.

19. The process of claim 15 wherein the lipase enzyme is pancreatic lipase and is used in combination with a pregastric lipase and a neutral bacterial protease.

20. The process of claim 1 wherein the product prior to or after enzyme inactivation is combined with from about 0.5% to about 1.2% ammonium phosphate.

21. The process of claim 7 which further includes the step of adding a member selected from the group consisting of:
   (a) cream; and
   (b) pasteurized milk or cream fermented with *L. casei*.

22. A product made by the process of claim 1.

23. The process of claim 1 wherein the product of Step (b) is preincubated for a period of time sufficient to partially digest the cheese or cheese curd.

24. The process of claim 7 wherein the neutral protease is a neutral fungal protease.

25. The process of claim 24 wherein the lipase is pancreatin.

26. The process of claim 15 wherein the lipase enzyme is pancreatic lipase and is used in combination with a neutral fungal protease.

27. The process of claim 1 wherein the product prior to or after enzyme inactivation is combined with from about 1.0% to about 2.5% of a food grade acid.

28. The process of claim 27 wherein the food grade acid is acetic acid.

* * * * *